(12) United States Patent
Nelson et al.

(10) Patent No.: US 6,529,377 B1
(45) Date of Patent: Mar. 4, 2003

(54) INTEGRATED COOLING SYSTEM

(75) Inventors: Richard D. Nelson, Austin, TX (US); Anjan Somadder, Fremont, CA (US)

(73) Assignee: Microelectronic & Computer Technology Corporation, Austin, TX (US)

( * ) Notice: Subject to any disclaimer, the term of this patent is extended or adjusted under 35 U.S.C. 154(b) by 0 days.

(21) Appl. No.: 09/946,798

(22) Filed: Sep. 5, 2001

(51) Int. Cl.[7] ................................................ H05K 7/20
(52) U.S. Cl. .................... 361/699; 29/890.03; 174/252; 165/104.33; 361/720; 361/749
(58) Field of Search ................................. 428/209, 901; 361/689, 703, 699–701, 705, 792, 717–720, 749–751; 257/713, 714; 174/16.3, 252; 165/46, 80.3, 80.4, 104.19, 104.33; 29/890.03

(56) References Cited

U.S. PATENT DOCUMENTS

| | | | | |
|---|---|---|---|---|
| 4,547,834 A | * | 10/1985 | Dumont et al. | 361/722 |
| 4,631,636 A | * | 12/1986 | Andrews | 361/699 |
| 4,734,315 A | * | 3/1988 | Spence-Bate | 428/209 |
| 4,774,630 A | * | 9/1988 | Reisman et al. | 361/718 |
| 5,142,441 A | * | 8/1992 | Seibold et al. | 361/689 |
| 5,317,478 A | * | 5/1994 | Sobhani | 361/689 |
| 6,015,607 A | * | 1/2000 | Fraivillig | 428/214 |

FOREIGN PATENT DOCUMENTS

| GB | 1105068 | * | 3/1968 | ................. 361/792 |

* cited by examiner

Primary Examiner—Gerald Tolin
(74) Attorney, Agent, or Firm—Fulbright & Jaworski, LLP

(57) ABSTRACT

Systems and methods are described for integrated cooling system. A method includes: circulating a liquid inside a flexible multi-layer tape; and transporting heat between a heat source that is coupled to the flexible multi-layer tape and a heat sink that is coupled to the flexible multi-layer tape. A method includes installing a flexible multi-layer tape in an electrical system, wherein the flexible multi-layer tape includes a top layer; an intermediate, layer coupled to the top layer; and a bottom layer coupled to the intermediate layer, the intermediate layer defining a closed loop circuit for a circulating fluid. An apparatus includes a flexible multi-layer tape, including: a top layer; an intermediate layer coupled to the top layer; and a bottom layer coupled to the intermediate layer, wherein the intermediate layer defines a closed loop circuit for a circulating fluid.

22 Claims, 4 Drawing Sheets

INTEGRATED COOLING SYSTEM

BACKGROUND OF THE INVENTION

1. Field of the Invention

The invention relates generally to the field of cooling and heat sinking. More particularly, the invention relates to an integrated liquid cooling system of flexible structure.

2. Discussion of the Related Art

It has been apparent for at least the past 15 years that, as performance improves, there is a growing need for efficient heat dissipation of electronic devices and systems. This trend has remained within the capabilities of air cooling until recently. However, some of today's typical desktop and mobile electronic systems can easily outstrip the cooling capability of existing air cooling techniques. Portable computers have begun challenging traditional thermal management systems.

Air cooling has shown limitations in certain high-power/high-dissipation applications mostly due to the fact that, in a typical situation, heat must be completely removed from an electronic system's enclosure.

On-chip and near-chip refrigeration techniques, such as thermo-electrics. reject a great amount of localized heat, which must also be transported out of the electronic package and its neighborhood. Furthermore, even though air cooling advances will continue to appear, it is known to one skilled in the art that liquid cooling technologies have a much greater capacity (than air cooling technologies) to handle large quantities of heat in small spaces.

A few techniques for integration of liquid cooling with chips have been available since the early 80's. The micro-channel cooling techniques of Tucherman and Pease were shown to be capable of handling high heat flux levels, at least 50 watts per square centimeter at the chip, with only small water flow requirements. Later work has confirmed and reproduced these heat sinks, but commercial applications have not been made. This results from limitations imposed by the integration itself. The micro-channels must be machined in the backside of the wafer or chip to be cooled and the technique does not provide for integrated liquid packaging and delivery systems.

A recent report describes micro-channels formed in aluminum nitride to cool a multichip module (MCM). However, the assembly terminates with conventional tubing fittings at the fluid manifold ends. Thus, using this technique would require the electronic system to include external tubing and pumps.

Heretofore, the mass flow capability of air cooling is incompatible with densely packed or high power dissipation electronics, and the "plumbing requirement" and potential for leaks and spills associated with liquid cooling has restricted its utility.

Another typical problem with liquid cooling technology has been miniaturization. Only one aspect of liquid cooling systems has been miniaturized or integrated to the scale of microelectronics, namely the heat exchanger at a hot chip. The prospect of assembling macro-scale pumps, tubes, and fittings, along with their potential for leaks, has stopped most efforts in liquid cooling technology development. What is needed is an integrated, liquid cooling system with micro-scale components based on flexible circuitry materials technology that solves these problems.

Heretofore, the requirement of providing an integrated liquid cooling system, with micro-scale components based on flexible circuitry materials technology for heat dissipation of high power, densely packaged electronic systems as referred to above have not been fully met. What is needed is a solution that addresses this requirement.

SUMMARY OF THE INVENTION

There is a need for the following embodiments. Of course, the invention is not limited to these embodiments.

According to an aspect of the invention, a method comprises: circulating a liquid inside a flexible multi-layer tape; and transporting heat between a heat source that is coupled to the flexible multi-layer tape and a heat sink that is coupled to the flexible multi-layer tape. According to another aspect of the invention, a method comprises installing a flexible multi-layer tape in an electrical system, wherein the flexible multi-layer tape includes a top layer; an intermediate layer coupled to the top layer; and a bottom layer coupled to the intermediate layer, the intermediate layer defining a closed loop circuit for a circulating fluid. According to another aspect of the invention, an apparatus comprises a flexible multi-layer tape, including a top layer: an intermediate layer coupled to the top layer; and a bottom layer coupled to the intermediate layer, wherein the intermediate layer defines a closed loop circuit for a circulating fluid.

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The drawings accompanying and forming part of this specification are included to depict certain aspects of the invention. A clearer conception of the invention, and of the components and operation of systems provided with the invention, will become more readily apparent by referring to the exemplary, and therefore nonlimiting, embodiments illustrated in the drawings, wherein like reference numerals (if they occur in more than one view) designate the same elements. The invention may be better understood by reference to one or more of these drawings in combination with the description presented herein. It should be noted that the features illustrated in the drawings are not necessarily drawn to scale.

DESCRIPTION OF PREFERRED EMBODIMENTS

Figure 1:
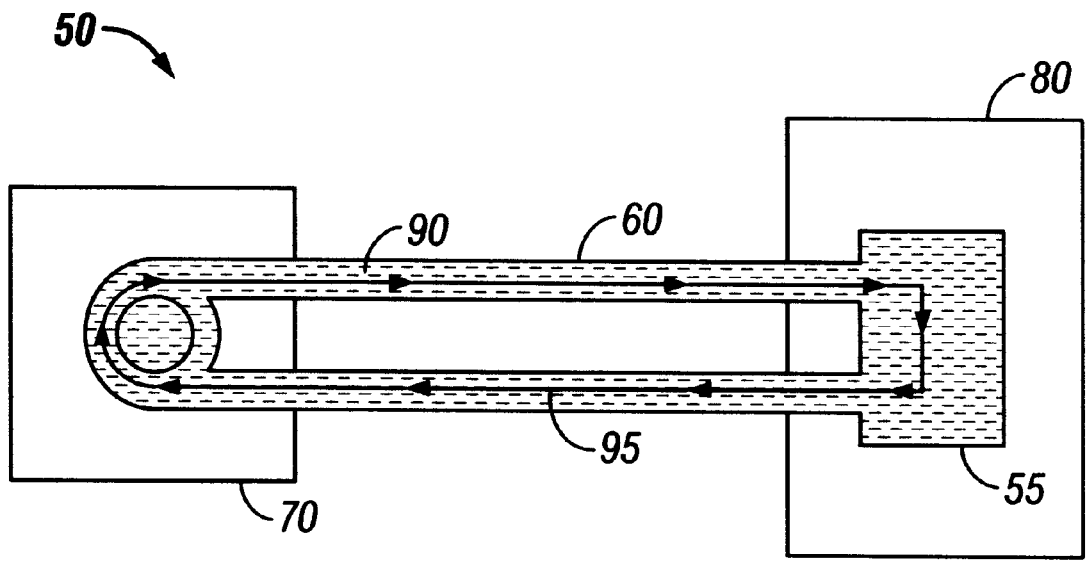
FIG. 1 is a block diagram of an integrated cooling system, representing an embodiment of the invention.

The invention and the various features and advantageous details thereof are explained more fully with reference to the nonlimiting embodiments that are illustrated in the accompanying drawings and detailed in the following description. Descriptions of well known components and processing techniques are omitted so as not to unnecessarily obscure the invention in detail. It should be understood, however, that the detailed description and the specific examples, while indicating preferred embodiments of the invention, are given by way of illustration only and not by way of limitation. Various substitutions, modifications, additions and/or rearrangements within the spirit and/or scope of the underlying inventive concept will become apparent to those skilled in the art from this detailed description.

The invention relates to an integrated liquid cooling system, and provides a method of liquid cooling and chip-level heat dissipation. An embodiment of the invention utilizes flexible circuitry materials technology. Flexible micro-channels and ducts are used to transport a cooling liquid, which extracts heat from a chip, moves it some distance out of the densely packed electronics area, and dumps it to the environment (usually room air). Liquids, especially water, have high enough specific heat and density to efficiently move the heat generated by electronic components.

In its integrated form, the flexible cooler includes miniature pumps, valves, piping, and cooling fins, resulting in a completely sealed, flexible liquid cooling system. The components utilized in this system are integrated with flexible metal and polymer laminates, in the form of a laminated tape. Used in conjunction with a local heat exchange component, the flexible liquid cooler completes the cooling chain required to dissipate the heat originated from a source.

Using flexible channels to transport a liquid, the invention can be advantageously employed in a variety of high power dissipation and space-constrained applications. In particular, the integrated cooling system and method can be utilized in electronic applications with high power dissipation and confined to close quarters (e.g. optical emitters, server forms, etc.). The micro-sized heat exchange apparatus generally provides a liquid handling assembly which could be readily bent and twisted on route to the final heat rejection area. A flexible, laminated metal/polymer/metal tape can be formed to provide the embodiments describer here.

An embodiment of the invention is represented by a closed loop liquid micro-cooling system based on mini-scale components, integrated and fully sealed. The closed liquid micro-cooling system comprises a flexible laminated metal/polymer/metal liquid loop piping, an external heat sink, an internal heat exchanger, and an internal mini-pump to enable the use of known micro-channel and micro-impingement techniques at the chip level. A suitable micro-fabrication technology, in a known manner, is generally employed to fabricate the chip-scale or miniature device of the invention useful for a variety of electronic and opto-electronic applications. The geometric features or materials used for these various components can be readily devised to suite a particular specification using a conventional micro-fabrication process from 3M corporation of Minneapolis/St. Paul, Minn. The invention should, however, not be restricted to the field of these applications, geometric features or materials, as will be readily evident.

A patterned and laminated copper sheet with a polyimide web can be produced with techniques already used in the production of flexible circuitry and TAB tape, and specially "multi-layer" tape. These include die cutting for the polyimide and subtractive etching of the copper. Small features can be produced in the polyimide by laser ablation. While flexible circuitry employs flat copper sheets, the particular needs of these cooling components may benefit from adding dimples, ridges, or bends to the copper in a forming step. Also, since there may be top and bottom layers of copper (with a polyimide layer in between), it may be desirable to join them at certain points by soldering or by plating via holes in the metal/polyimide/metal stack. All of these structures and processes are within the capability of the state of the art.

Fins may be required on the copper layers at heat exchange regions, either where heat is to be absorbed at a package, or where it is to be rejected to external cooling air. Both longitudinal fins and pin fins can be produced by plating through openings in the polyimide web. They can also be produced by plating through openings formed in photoresist. Several other methods exist for adding pin fins, for instance in a pick-and-place "surface mount" operation followed by solder reflow.

In general, the fin thickness or diameter and the fin spacing is desired to be relatively small on the order of 50 microns (micro-channels) to 500 microns (milli-channels). Use of such small fins and channel dimensions inherently increases the heat transfer coefficient on the exposed surfaces. As a result, coolant flow rates may be expected to be relatively small on the order of a few cubic centimeters per second.

Many factors such as design specifications, balancing liquid flow, pressure drop, heat load, and temperature rise may determine optimal fin and channel dimensions for a particular application. An integrated pumping system may move fluids at the rate of a few cubic centimeters per second or higher. The total pressure requirement ranges from a fraction of a pound per square inch to 20 pounds per square inch.

Inside the flexible piping system, the cooling liquid may be desired to flow in a particular direction, and valves can be used for that purpose. Miniature flow-operated check valves can be devised using simple ball-checks, diaphragm operated poppets, or flappers created in the polyimide web. Magnetically driven valves can be used as an alternative.

A micro-pump can include a small rotor in a rotor housing created in the polyimide web. For instance, a micro-mechanical gear pump can be implemented, using externally rotating magnetic fields to couple the driving energy to the gears. Lubrication, sealing, and micro-mechanical bearings may be also provided.

Referring to FIG. 1, a block diagram of an integrated cooling system 50 is depicted. The integrated cooling system 50 integrates liquid pumping, delivery, and heat exchange functionality to transmit heat generated form a problem area at a particular location to a heat rejection area. For example, the integrated cooling system 50 could be coupled to a heat source 80 for transporting heat generated to a substantially spaced apart location in the heat rejection area. To integrate liquid cooling in a flexible manner, the integrated cooling system 50 may comprise a flexible liquid conduit 60, an integrated pumping unit 70, and an integrated heat-exchanging unit 55.

In operation, the flexible liquid conduit 60 may provide liquid ducting and manifolding between the integrated pumping unit 70 and the integrated heat exchanging unit 55. The integrated pumping unit 70 may provide fluid circulation within the integrated cooling system 50. A liquid 90 such as a coolant or water can flow in a closed loop path 95 for dissipating heat generated in the heat source 80.

Figure 2:
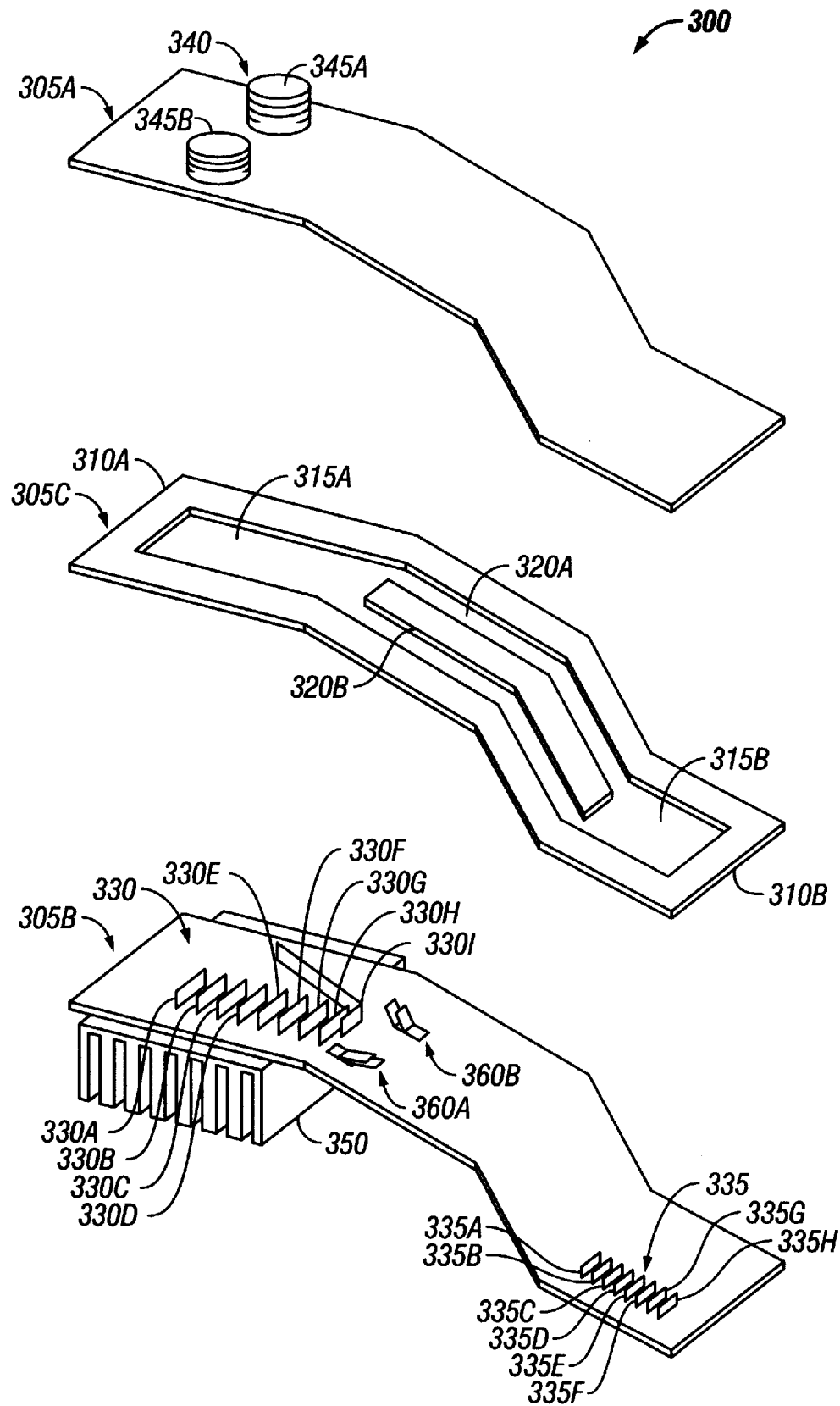
FIG. 2 is an exploded perspective view of a flexible integrated cooling system, representing an embodiment of the invention.

Referring to FIG. 2, an exploded perspective view of a flexible integrated cooling system 300 is depicted. The flexible integrated cooling system 300 may comprise three layers including a top metal layer 305A, a bottom metal layer 305B, and a center layer 305C that is generally disposed therebetween. The top and bottom metal layers 305A, 305B can be made of copper, which is a good thermal conductor. The center layer 305C may be a spacer such as a plastic core of an appropriate thickness. For example, a polyimide core on the order of from 5 mils to as much as 50 mils may be utilized. Alternatively, the center layer 305C comprising a foamed material is also contemplated.

Among other characteristics, flexibility and patternability are primary characteristics for the center layer 305C. As can be seen, the center layer 305C may be patterned on a first distal end 310A to provide a left cavity 315A and on a second distal end 310B with a right cavity 315B. Furthermore, one or more micro-channels may couple the left and right cavities 315A and 315B. For example, a first tube 320A may be patterned to connect the left cavity 315A to the right cavity 315B. Likewise, a second tube 320B connecting the right cavity 315B to the left cavity 315A may be utilized. The first and second tubes 320A, 320B form a closed loop circuit for a liquid to flow when the center layer 305C is suitably enclosed at the top and bottom utilizing the top and bottom metal layers 305A, 305B, respectively. Accordingly, the three layers 305A through 305C may be glued together to form a multi-layer metal tape which provides a flexible cooling interconnect for the integrated system 300 to handle an encapsulated liquid while exchanging heat in a self-contained manner.

In order to enhance heat transfer within the left and right cavities 315A, 315B, a first set of fins 330 and a second set of fins 335 may be incorporated therein, respectively. The first and second sets of fins 330 and 335 are equally spaced from each other and separated by intermediate channels. Accordingly, for heat dissipation within the left cavity 315A, a plurality of fins 330A through 330l may be suitably incorporated. Likewise, for heat extraction within the right cavity 315B, a plurality of fins 335A through 335H may be appropriately included. If the cavities 315A, 315B are spaced significantly proximal to each other and if the center layer 305C is relatively thin, fins 330 and 335 may be discarded.

An external pump 340 can be attached to the top metal layer 305A. The external pump 340 may comprise a pair of bellows including, a first bellow 345A and a second bellow 345B to provide a push-pull action for guiding the encapsulated liquid to flow through the closed loop circuit. Such oscillatory push-pull action generally causes a net fluid flow of the encapsulated liquid in a desired direction. Alternatively, the left cavity 315A may include an internal pump such as a rotary pump, a diaphragm pump, or an electrokinetic pump. It is to be understood that a variety of pumping means may be readily devised. Optionally, to reject heat to atmosphere, an external heat sink 350 may be attached proximal to the left cavity 315A. As the fluid is desired to flow from one cavity to the other and back, to control such flow one or more valves may be deployed. For example, a pair of flapper valves 360A and 360B may allow flow of the encapsulated liquid in a desired direction.

The foregoing describes only one embodiment of the present invention, however, many variations of this embodiment will be obvious to a person skilled in the art of semiconductor or micro-electromechanical fabrication. Certainly, various other materials and techniques can be utilized in the construction of the various layers.

In operation, the encapsulated liquid is generally confined to flow through micro-channels including the first and second tubes 320A and 320B formed in the polyimide core of center layer 305C, which is generally bounded by the two opposing copper sheets of the first and second layers 305A and 305B. The exploded view of FIG. 2 shows the flexible integrated cooling system 300 with flexible micro-channels, generally bent to carry the encapsulated liquid between a hot area on a second distal end 310B and a cooled area on a first distal end 310A. Known die cutting, chemical etching, and laser ablation techniques can be readily employed to cut out regions in the polyimide core to define plenums or pipes, including the depicted first and second tubes 320A and 320B. Also, a variety of known techniques including plating techniques could be utilized to form fins 330. 335 on the lower copper plane of the bottom layer 305B.

While the pair of flapper valves 360A and 360B are shown as spot-welded, numerous alternate techniques could be used such as adhesively bonding assemblies. Further, the bellows pair of the external pump 340 may be soldered on the top layer 305A for externally actuating first and second bellows 345A and 345B in a push-pull mode to move fluid in the direction permitted by internal flappers valves 360A and 360B. Using suitable geometry for the fins 330 and 335, liquid flows of a desired level could be contemplated, such as liquid flows of a few cubic centimeters per second may be provided. Heat is generally rejected to external air by convection on the metal surfaces of the top and bottom layers 305A, 305B and, additionally or optionally through the attached heat sink 350.

Figure 3:
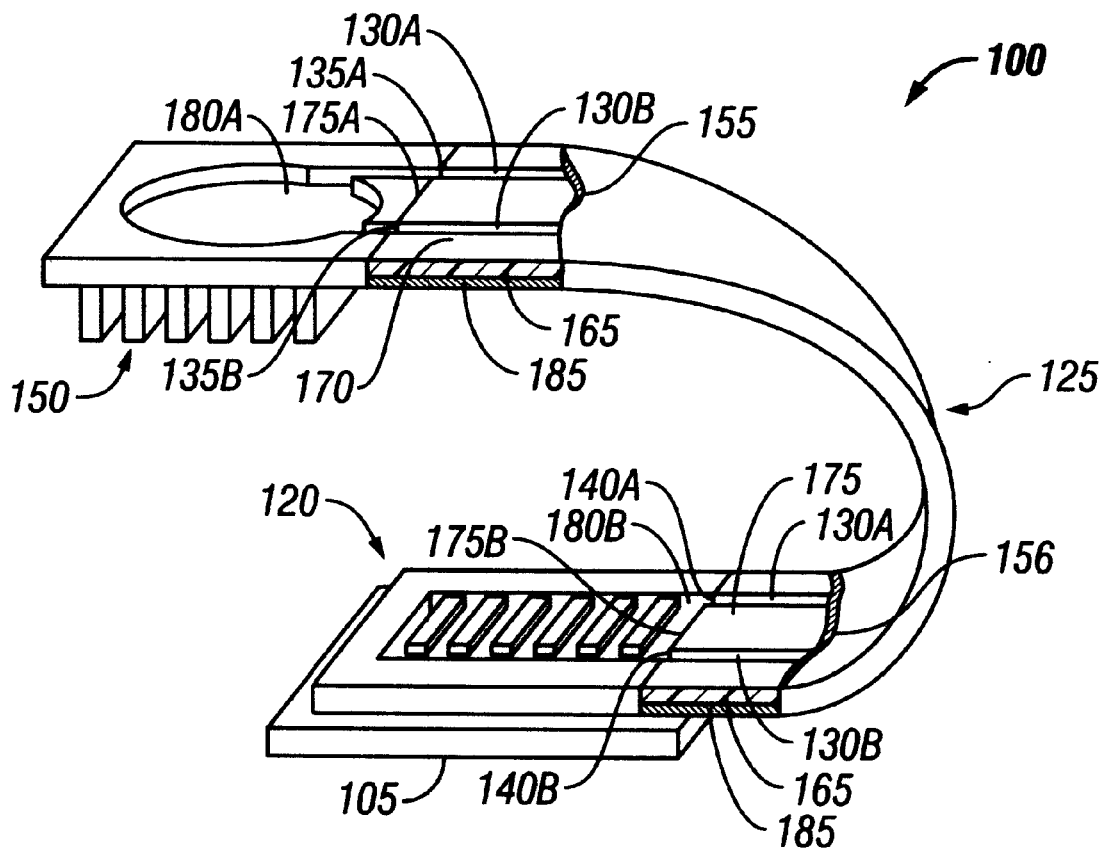
FIG. 3 is a perspective view of a flexible integrated cooling system, representing an embodiment of the invention.

Referring to FIG. 3, a perspective view, partially in cross section of an exemplary a embodiment of an integrated flexible liquid cooler is depicted. With reference to FIG. 1 and FIG. 3, for dissipating heat generated in a package 105, an integrated flexible liquid cooler 100 may comprise a first cavity 180A to contain a pump for providing circulation of the liquid 90, and a heat exchanger 120 disposed adjacent to the package 105 in a heat conducting relationship for extracting heat therefrom. For providing transpiration for the liquid 90, an integrated flexible liquid cooler 100 may further include a flexible housing 125 having a first pipe 130A and a second pipe 130B. The first and second pipes 130A and 130B may comprise respective first ends 135A, 135B and respective second ends 140A, 140B. The first ends 135A, 135B may be securely coupled to the first cavity 180A and the second ends 140A, 140B could be coupled to the heat exchanger 120 to form the closed loop path 95 for circulating the liquid 90.

The integrated flexible liquid cooler 100 may further comprise a heat sink 150 coupled to the first cavity 180A in a heat conducting relationship for dissipating the heat generated in the package 105. The package 105 may comprise one or more electronic components having substantially high power dissipation. While the package 105 may be disposed at a location having substantially constrained airflow, heat generated by the package 105 could be readily transferred for dissipation from the heat exchanger 120 to the heat sink 150 via a fluid flow through the flexible housing 125. The invention is particularly advantageous when the first cavity 180A is integrated with heat sink 150, which can be located away from the package 105 so that the extracted heat may be remotely dissipated.

The flexible housing 125 may comprise a first layer 155, an intermediate layer 165, and a second layer 185. The intermediate layer 165 may include a first and a second opposing portions 175A, 175B, respectively. It may also include the first cavity 180A at the first portion 175A, and a second cavity 180B at the second portion 175B. Moreover, the intermediate layer 165 is tightly coupled to the first major surface 170 of the first layer 155. The intermediate layer 165 is also coupled to the second surface 171 of the second layer 156.

The first layer 155 and the second layer 156 may be made of a metal such as copper. Moreover, the intermediate layer 165 is flexible, patternable, and may comprise a foamed polymer or a polyimide layer. The first and second pipes 130A and 130B may couple the first cavity 180A to the second cavity 180B, and may be formed by appropriately patterning the intermediate layer 165. The cavity 180A may contain a pump to provide the circulation of a liquid, routing it through a closed loop path. As shown in FIG. 3 the first cavity 180A can contain a pump to be integrated with the flexible housing 125. Likewise, the heat exchanger 120 can be internally located at the second cavity 180B.

One skilled in the art will realize that a variety of pumps could be deployed including, but are not limited to a rotary pump or a diaphragm pump. Such rotary or diaphragm pump circulate a liquid, thereby causing a net flow thereof through a closed loop path between the first cavity 180A and the second cavity 180B.

Figure 4:
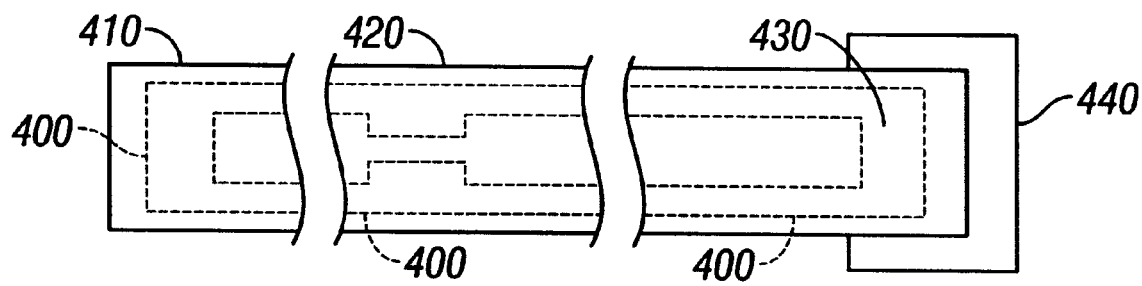
FIG. 4 is a section view of a heat transfer system, representing an embodiment of the invention.

Referring to FIG. 4, a heat transfer system is depicted. A pumping region 410 is coupled to a heat rejection region 420 via a fluid micro-channel 400. The heat rejection region 420 is coupled to a heat extraction region 430 via the fluid micro-channel 400. The heat extraction region 430 is coupled to a heat source 440.

Still referring to FIG. 4, three general regions are shown: the heat extraction region 430, the heat rejection region 420, and the pumping region 410. These are created and interconnected by fluid micro-channel 400 in the tape core. The heat extraction 430 region will generally be remote and separate from the heat rejection region 420 and the pumping region 410. However, the latter two may be in the order shown, reversed in order, or combined into a single region Referring to FIG. 5, a gear pump with magnetic coupling is depicted. A fluid channel 500 in the tape core allows liquid to circulate in the flexible tape. A ferromagnetic gear 510 is coupled to a gear 505 inside the fluid channel 500 in the tape core. An external coil 520 drives the ferromagnetic gear 510.

Figure 5:
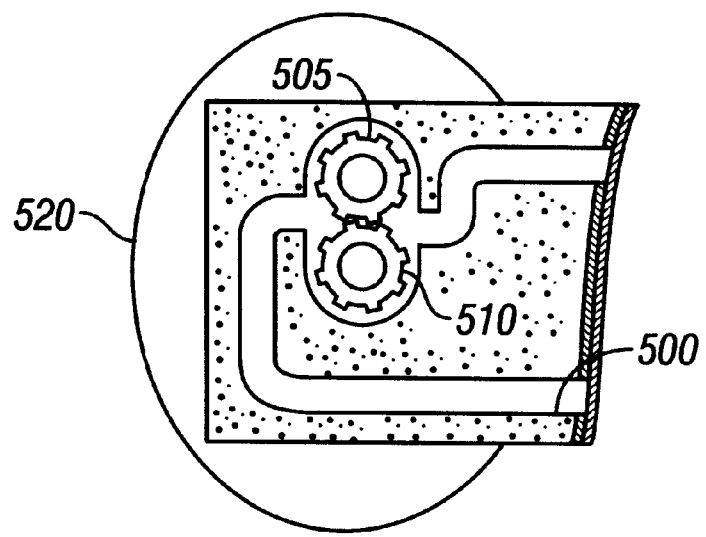
FIG. 5 is a diagram of a gear pump with magnetic coupling, representing an embodiment of the invention.

Still referring to FIG. 5, pump systems of this type are well known, but have not been integrated with a tape based cooling system in the prior art. One of the gears is ferromagnetic, or made of a permanent magnetic material, and is driven by a rotating magnetic field created by the external coil 520 (shown below the tape itself). FIG. 5 is a view of the tape with the top copper sheet removed. The gears have holes in their centers and are simply placed on bearing posts created in the tape core (polyimide) by laser ablation.

Referring to FIGS. 6A–6D, various heat transfer regions of different types of flexible tape are depicted. Several fin structures are shown, which enhance heat transfer to the fluid passing through them.

Figure 6A:
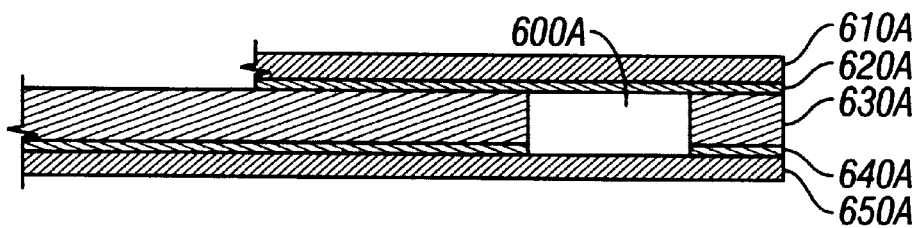
FIGS. 6A–6D are section views of heat transfer regions, representing an embodiment of the invention.

Referring to FIG. 6A, a fluid micro-channel 600A is patterned in a foam layer 630A. A polyimide layer 610A is coupled to the foam layer 630A via an adhesive layer 620A. The foam layer 630A is coupled to a metal layer 650A via an adhesive layer 640A.

Still referring to FIG. 6A, a heat transfer region of a copper/foam/polyimide flexible tape with adhesive between layers is depicted. If heat transfer is desired only through the bottom surface, the upper surface need not be copper and can be another material, such as polyimide. This makes the assembly even more flexible.

Figure 6B:
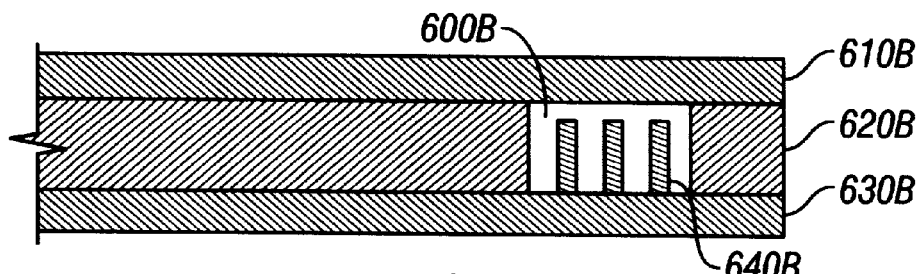

Referring to FIG. 6B, a fluid micro-channel 600B is patterned in a thermoplastic layer 620B. A metal layer 610B is coupled to the thermoplastic layer 620B. The thermoplastic layer 620B is coupled to a metal layer 630B. A set of fins 640B is plated to the metal layer 630B, inside the fluid micro-channel 600B.

Still referring to FIG. 6B, a heat transfer region of a copper/thermoplastic/copper flexible tape is depicted. Melting the thermoplastic provides the bond to the copper. Also shown is a possible heat transfer structure using micro-fins plated on one of the copper layers.

Figure 6C:
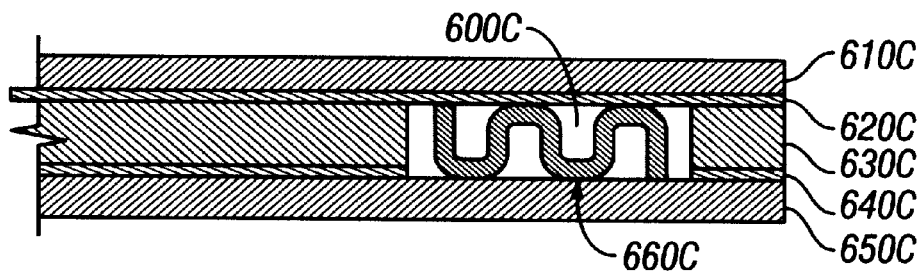

Referring to FIG. 6C, a fluid micro-channel 600C is patterned in a polyimide layer 630C. A metal layer 610C is coupled to the polyimide layer 630C via an adhesive layer 620C. The polyimide layer 630C is coupled to a metal layer 650C via an adhesive layer 640C. A set of folded metal fins 660C is attached to the metal layer 650C via welding, gluing or soldering, inside the fluid micro-channel 600C.

Figure 6D:
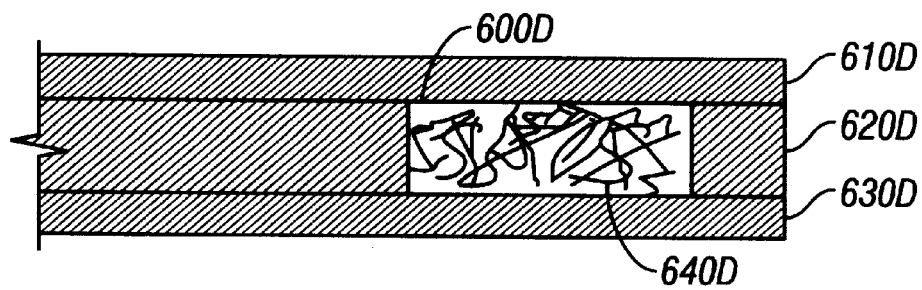

Referring to FIG. 6D, a fluid micro-channel 600D is patterned in a polyimide layer 620D. A metal layer 610D is coupled to the polyimide layer 600D. The polyimide layer 620D is coupled to a metal layer 630D. A metal mesh 640D partially fills the fluid micro-channel 600D.

Variations of the invention can be devised by one skilled in the art. For example, micro-channel fins can be machined on a chip surface. A tape based cooling system may provide piping and manifolding, and can be soldered or adhesively sealed to the chip surface to form an integrated package/liquid loop. Another implementation utilizes two polyimide layers and three metal layers to provide fluid piping and plenums. The intermediate layer is perforated at the heat exchange regions to provide liquid jet impingement cooling. In yet another implementation, the one of the two polyimide ducts is filled with a wick, the other is a vapor channel. A plurality of layers may be utilized.

The context of the invention can include cooling and/or heat sinking electronic components, subsystems and/or systems. The context of the invention can also include cooling and/or heat sinking mechanical, optical, chemical and/or biological components, subsystems and/or systems.

The invention can also be included in a kit. The kit can include some, or all, of the components that compose the invention. The kit can be an in-the-field retrofit kit to improve existing systems that are capable of incorporating the invention. The kit can include software, firmware and/or hardware for carrying out the invention. The kit can also contain instructions for practicing the invention. Unless otherwise specified, the components, software, firmware, hardware and/or instructions of the kit can be the same as those used in the invention.

The term approximately, as used herein, is defined as at least close to a given value (e.g., preferably within 10% of, more preferably within 1% of, and most preferably within 0.1% of). The term substantially, as used herein, is defined as at least approaching a given state (e.g., preferably within 10% of, more preferably within 1% of, and most preferably within 0.1% of). The term coupled, as used herein, is defined as connected, although not necessarily directly, and not necessarily mechanically. The term deploying, as used herein, is defined as designing, building, shipping, installing and/or operating. The term means, as used herein, is defined as hardware, firmware and/or software for achieving a result.

The term program or phrase computer program, as used herein, is defined as a sequence of instructions designed for execution on a computer system. A program, or computer program, may include a subroutine, a function, a procedure, an object method, an object implementation, an executable application, an applet, a servlet, a source code, an object code, a shared library/dynamic load library and/or other sequence of instructions designed for execution on a computer system. The terms including and/or having, as used herein, are defined as comprising (i.e., open language). The terms a or an, as used herein, are defined as one or more than one. The term another, as used herein, is defined as at least a second or more.

Advantages of the Invention

An integrated liquid cooling system of flexible structure, representing an embodiment of the invention, can be cost effective and advantageous for at least the following reasons. The invention allows for a thin, bendable, potentially resilient heat transport system. The invention improves quality and/or reduces costs compared to previous approaches.

All the disclosed embodiments of the invention disclosed herein can be made and used without undue experimentation in light of the disclosure. Although the best mode of carrying out the invention contemplated by the inventors is disclosed, practice of the invention is not limited thereto. Accordingly, it will be appreciated by those skilled in the art that the invention may be practiced otherwise than as specifically described herein.

Further, the individual components need not be formed in the disclosed shapes, or combined in the disclosed configurations, but could be provided in virtually any shapes, and/or combined in virtually any configuration. Further, the individual components need not be fabricated from the disclosed materials, but could be fabricated from virtually any suitable materials.

Further, although the integrated liquid cooling system of flexible structure described herein can be a separate module, it will be manifest that the integrated liquid cooling system of flexible structure may be integrated into the system with which it is associated. Furthermore, all the disclosed elements and features of each disclosed embodiment can be combined with, or substituted for, the disclosed elements and features of every other disclosed embodiment except where such elements or features are mutually exclusive.

It will be manifest that various substitutions, modifications, additions and/or rearrangements of the features of the invention may be made without deviating from the spirit and/or scope of the underlying inventive concept. It is deemed that the spirit and/or scope of the underlying inventive concept as defined by the appended claims and their equivalents cover all such substitutions, modifications, additions and/or rearrangements.

The appended claims are not to be interpreted as including means-plus-function limitations, unless such a limitation is explicitly recited in a given claim using the phrases(s) "means for" and/or "step for." Subgeneric embodiments of the invention are delineated by the appended independent claims and their equivalents. Specific embodiments of the invention are differentiated by the appended dependent claims and their equivalents.

What is claimed is:

1. A method, comprising:
    providing a flexible multi-layer tape including, a heat extraction region, a fluid ducting region, a fluid pumping region and a heat rejection region;
    circulating a liquid inside the flexible multi-layer tape; and
    transporting heat between a heat source that is coupled to the heat extraction region of the flexible multi-layer tape and a heat sink that is coupled to the heat rejection region of the flexible multi-layer tape.

2. The method of claim 1, wherein circulating the liquid inside the flexible multi-layer tape includes circulating the liquid inside the flexible multi-layer tape via a closed loop circuit.

3. The method of claim 1, wherein circulating the liquid inside the flexible multi-layer tape includes pumping the liquid inside the flexible multi-layer tape.

4. The method of claim 1, wherein circulating the liquid inside the flexible multi-layer tape includes circulating the liquid inside the flexible multi-layer tape in a preferred direction around the closed loop circuit via a plurality of valves.

5. The method of claim 1, wherein circulating the liquid includes circulating water.

6. The method of claim 1, wherein exchanging heat between the heat source and the heat sink includes flowing the liquid over a plurality of fins.

7. A method, comprising, installing a flexible multi-layer tape in an electrical system, the flexible multi-layer tape including, a top layer; an intermediate layer coupled to the top layer; and a bottom layer coupled to the intermediate layer, the intermediate layer defining a closed loop circuit for a circulating fluid, the flexible multi-layer tape having a heat extraction region, a fluid ducting region, a fluid pumping region and a heat rejection region;
    attaching the heat extraction region to an electronic component;
    attaching the heat rejection region to a heat sink; and
    coupling a pump to the pumping region.

8. The method of claim 7, further comprising providing a liquid within the closed loop circuit.

9. The method of claim 7, further comprising bending the multi-layer flexible tape.

10. An apparatus, comprising a flexible multi-layer tape, including:
    a top layer;
    an intermediate layer coupled to the top layer and defining a plurality of internal cavities forming a closed-loop circuit for circulating fluid, the plurality of internal cavities including a plurality of heat exchange devices; and
    a bottom layer coupled to the intermediate layer.

11. The apparatus of claim 10, wherein the top layer includes a metal layer.

12. The apparatus of claim 10, wherein the intermediate layer includes a polymer layer.

13. The apparatus of claim 10, wherein the bottom layer includes a metal layer.

14. The apparatus of claim 10, wherein the plurality or heat exchange devices include at least one member selected from the group consisting of: a longitudinal fin, a pin fin, a folded metal fin, and a metal mesh.

15. The apparatus of claim 10, wherein the closed loop circuit includes a heat extraction region, a pumping region and a heat rejection region.

16. The apparatus of claim 15, further comprising a pump coupled to the pumping region.

17. The apparatus of claim 16, wherein the pump includes at least one member selected from the group consisting of: a bellows pump, a rotary pump, and a micro-mechanical gear pump.

18. The apparatus of claim 16, wherein the pump is located in a cavity defined by the intermediate layer.

19. The apparatus of claim 10, further comprising a heat source coupled to the flexible multi-layer tape.

20. The apparatus of claim 19, wherein the heat source includes a plurality of electronic components.

21. The apparatus of claim 10, further comprising a heat sink coupled to the flexible multi-layer tape.

22. The apparatus of claim 21, wherein the heat sink includes a heat exchange unit.

* * * * *

UNITED STATES PATENT AND TRADEMARK OFFICE
CERTIFICATE OF CORRECTION

PATENT NO. : 6,529,377 B1
DATED : March 4, 2003
INVENTOR(S) : Nelson et al.

It is certified that error appears in the above-identified patent and that said Letters Patent is hereby corrected as shown below:

Column 10,
Line 55, please delete "or" and insert -- of -- therefor.

Signed and Sealed this

Sixth Day of May, 2003

JAMES E. ROGAN
*Director of the United States Patent and Trademark Office*